United States Patent
Simpson et al.

(10) Patent No.: US 11,076,761 B2
(45) Date of Patent: Aug. 3, 2021

(54) SCREENING TEST FOR DETECTION OF DEEP VEIN THROMBOSIS

(71) Applicants: Epworth Research Institute, Richmond (AU); La Trobe University, Bundoora (AU); Laurence Simpson, Richmond (AU); Lawrie Knuckey, Richmond (AU)

(72) Inventors: Laurence Simpson, Richmond (AU); Lawrie Knuckey, Richmond (AU); Paul Junor, Bundoora (AU)

(*) Notice: Subject to any disclaimer, the term of this patent is extended or adjusted under 35 U.S.C. 154(b) by 368 days.

(21) Appl. No.: 15/519,264

(22) PCT Filed: Oct. 15, 2015

(86) PCT No.: PCT/AU2015/050636
§ 371 (c)(1),
(2) Date: Apr. 14, 2017

(87) PCT Pub. No.: WO2016/058053
PCT Pub. Date: Apr. 21, 2016

(65) Prior Publication Data
US 2017/0231506 A1    Aug. 17, 2017

(30) Foreign Application Priority Data
Oct. 17, 2014    (AU) .................................. 2014904149

(51) Int. Cl.
*A61B 5/00*    (2006.01)
*A61B 5/02*    (2006.01)
(Continued)

(52) U.S. Cl.
CPC ........ *A61B 5/02007* (2013.01); *A61B 5/0024* (2013.01); *A61B 5/0048* (2013.01);
(Continued)

(58) Field of Classification Search
None
See application file for complete search history.

(56) References Cited

U.S. PATENT DOCUMENTS 6,002,965 A     12/1999   Katz et al.
6,132,385 A  *  10/2000   Vain ....................... A61B 5/103
                                                          600/553
(Continued)

FOREIGN PATENT DOCUMENTS

KR      20040095210      11/2004
KR        101442046       9/2014

OTHER PUBLICATIONS

"Change." Dictionary.com. 2020. Retrieved Sep. 24, 2020, from www.dictionary.com (Year: 2020).*
(Continued)

*Primary Examiner* — Matthew Kremer
*Assistant Examiner* — Samuel C Kim
(74) *Attorney, Agent, or Firm* — Onello & Mello, LLP (57) ABSTRACT

A system (100) for assessing a subject at risk of a soft tissue abnormality such as deep vein thrombosis (DVT), comprises a motion sensor (108) which is adapted to be fixed, in use, to a muscle (106) of the subject. The motion sensor includes a transmitter (206) configured to transmit a signal (400) representing motion of the sensor. A receiver (118) is configured to receive the signal from the transmitter of the motion sensor. A signal processor (112) is coupled to the receiver and configured to analyse first and second data sets received via the receiver from the motion sensor. The first and second data sets represent respective first and second oscillatory mechanical responses of first and second muscles of the subject resulting from mechanical stimuli. The analysis comprises determining first and second parameter sets characterising the first and second oscillatory mechanical (Continued)

responses, and comparing the first parameter set with the second parameter set to assess a possible presence of DVT in the subject.

14 Claims, 4 Drawing Sheets

(51) Int. Cl.
*A61B 5/11* (2006.01)
*G16H 50/30* (2018.01)
(52) U.S. Cl.
CPC .............. *A61B 5/11* (2013.01); *A61B 5/1107* (2013.01); *A61B 5/4519* (2013.01); *A61B 5/6828* (2013.01); *A61B 5/7257* (2013.01); *A61B 5/7275* (2013.01); *G16H 50/30* (2018.01); *A61B 2562/0219* (2013.01)

(56) References Cited

U.S. PATENT DOCUMENTS

| | | | |
|---|---|---|---|
| 6,226,552 B1 | 5/2001 | Staunton et al. | |
| 6,234,975 B1* | 5/2001 | McLeod | A61B 5/1036 600/552 |
| 6,980,852 B2 | 12/2005 | Jersey-Willuhn et al. | |
| 7,169,107 B2 | 1/2007 | Jersey-Willuhn et al. | |
| 7,184,820 B2 | 2/2007 | Jersey-Willuhn et al. | |
| 2003/0163061 A1 | 8/2003 | Miyoshi et al. | |
| 2004/0267331 A1* | 12/2004 | Koeneman | A61N 1/36003 607/49 |
| 2006/0085047 A1 | 4/2006 | Unsworth et al. | |
| 2007/0038392 A1* | 2/2007 | Iyer | G01M 15/12 702/56 |
| 2009/0005834 A1 | 1/2009 | Weintraub et al. | |
| 2010/0094175 A1* | 4/2010 | Hovorka | A61B 5/0048 600/587 |
| 2012/0065561 A1* | 3/2012 | Ballas | A61H 9/0021 601/152 |
| 2013/0289365 A1* | 10/2013 | Vain | A61B 5/4519 600/301 |
| 2015/0038879 A1* | 2/2015 | Peipsi | A61B 5/442 600/587 |
| 2015/0374275 A1* | 12/2015 | Peipsi | A61B 5/0053 600/587 |

OTHER PUBLICATIONS

International Search Report dated Jan. 18, 2016 issued in International Application No. PCT/AU2015/050636.
Extended European Search Report dated Feb. 22, 2018, issued in corresponding European Application No. 15850063.7.

* cited by examiner

SCREENING TEST FOR DETECTION OF DEEP VEIN THROMBOSIS

FIELD OF THE INVENTION

The present invention relates to systems, methods and apparatus for assisting healthcare workers in the screening and detection of abnormalities and pathological states in soft tissue, and has particular application at least, but not confined to, the screening and detection of deep vein thrombosis (DVT) of the lower limbs.

BACKGROUND OF THE INVENTION

Deep vein thrombosis (DVT) is a significant complication in all surgical and medical wards, as well as in other aspects of community life. It is a condition that has significant implications for pulmonary embolism, and possible death. There are also dangers of continuing morbidity in the legs, and also in the lungs, from the presence of venous thromboembolism.

Currently, there is no recognised clinical assessment for DVT that has an accuracy greater than 60 percent, and many patients with DVT have no overt clinical findings.

In cases of suspected DVT, it is necessary to undertake specific investigations for confirmation. These investigations are expensive, and include techniques such as Doppler ultrasonography which requires significant equipment and expertise. Tests for pulmonary embolism may also be necessary, involving methods such as computed tomography (CT) or chest scanning using a radioactive marker. Blood tests may also be performed. As will be appreciated, a number of these tests are invasive and/or uncomfortable for the patient. Many of these tests cannot be performed at the bedside.

A particular concern is that many patients develop DVT with minimal or no significant changes or symptoms (e.g. pain and swelling), and as a result many patients are sent home early following surgery without any assessment of the possibility of DVT. Deaths from complications of venous thromboembolism have been known to result in such cases.

There is, accordingly, a pressing need for a reproducible, objective investigation that can be performed by a trained technician, a trained clinician, or other healthcare worker. Ideally, assessment of the possible presence of DVT should be able to be conducted simply, with high reliability, at relatively low cost, and without the requirement for invasive or uncomfortable procedures. The present invention seeks to address these requirements.

SUMMARY OF THE INVENTION

In one aspect, the present invention provides a system for assessing a subject at risk of a soft tissue abnormality such as deep vein thrombosis (DVT), comprising:

a motion sensor, adapted to be fixed, in use, to a muscle of the subject, the motion sensor including a transmitter configured to transmit a signal representing motion of the sensor;

a receiver, configured to receive the signal from the transmitter of the motion sensor; and a signal processor, coupled to the receiver, and configured to analyse first and second data sets received via the receiver from the motion sensor, the first and second data sets representing respective first and second oscillatory mechanical responses of first and second muscles of the subject resulting from mechanical stimuli, wherein the analysis comprises determining first and second parameter sets characterising the first and second oscillatory mechanical responses, and comparing the first parameter set with the second parameter set to assess a possible presence of DVT in the subject.

For convenience of description, where the term 'muscle' is employed in this specification (including in the appended claims), this should be understood to encompass a single muscle, or one or more muscles comprising a muscle group.

Embodiments of the invention take advantage of the observation that, upon clinical examination, in certain pathological states there is a change in the calf muscles that may be identified in a response to a percussive stimulus applied to the tissues. In DVT, it has been observed that the normal mobility of the calf is reduced. It has thus been observed that tapping the calf, which under normal circumstances has considerable mobility like the bounce of jelly, results in a more 'dough-like' response in the presence of DVT. It has been found, however, that skill and experience are required in order to master the use of this technique for the detection of DVT. It is reasonably anticipated that similar effects will also occur in comparable pathological states of other soft tissues.

Embodiments of the invention further take advantage of the fact that disorders such as DVT are normally present in only one comparable muscle of the subject. Thus, for example, if a DVT is present in the right calf muscle, the response of this muscle to a mechanical stimulus should be different from the response of the subject's left calf muscle, in which DVT is unlikely to be present.

Embodiments of the present invention therefore advantageously employ a consistent, reproducible, objective analysis technique, comprising determining and comparing suitable parameter sets of corresponding pairs of muscles of the subject, in order to detect significant differences indicative of the possible presence of DVT or other abnormality.

Accordingly, in embodiments of the invention the first and second muscles are corresponding muscles of respective left and right limbs of the subject. Particularly, the first and second muscles are left and right calf muscles of the subject.

Embodiments of the invention decompose the oscillatory mechanical responses of the first and second muscles, such that the first and second parameter sets each comprise at least one frequency parameter and at least one corresponding damping parameter characterising the oscillatory mechanical response. Typically, the first and second parameter sets each comprise frequency parameters and corresponding damping parameters of two or more oscillatory components of the mechanical responses of the first and second muscles of the subject.

According to embodiments of the invention, a possible presence of DVT in the subject is assessed based on a difference between the frequency parameters and/or the damping parameters of the first and second parameter sets. For example, a lower frequency response and/or more rapid damping in one of the first and second muscles, as compared with the other, is indicative of the possible presence of DVT in the subject. The frequency response may typically be a resonant frequency, while damping may be measured as a damping factor.

For the purpose of comparing the first parameter set with the second parameter set, the signal processor may be configured to present information relating to the first and second parameter sets on a display, for evaluation and further diagnostic consideration, by an operator such as a trained technician, trained clinician, or other healthcare worker.

In other embodiments, further statistical analysis of the first and second parameter sets, obtained over multiple responses of the first and second muscles of the subject to multiple mechanical stimuli, may be performed in order to assess the statistical and/or clinical significance of differences between the first and second parameter sets, and to provide a specific indication, such as a likelihood or probability of the presence of an abnormality such as DVT in the subject.

According to embodiments of the invention, the motion sensor comprises an accelerometer. Advantageously, the accelerometer comprises a multi-axis accelerometer, such as a two-axis or three-axis accelerometer.

In some embodiments, a communications channel between the transmitter and the receiver comprises a wired connection.

In other embodiments, a communications channel between the transmitter and the receiver comprises a wireless connection. Advantageously, the use of a wireless connection between the motion sensor and the signal processor avoids the possibility that the presence of physical connections may influence the mechanical response of the first and second muscles resulting from the applied mechanical stimuli.

In various embodiments, the signal communicated from the transmitter to the receiver may be an analog signal, which may be sampled and digitised at the receiver, or may be a digital signal, having been sampled and digitised at the motion sensor.

In another aspect, the invention provides an apparatus for assessing a subject at risk of DVT, comprising:

a receiver, configured to receive a signal from a transmitter associated with a motion sensor, wherein the motion sensor is adapted to be fixed, in use, to a muscle of the subject, and is configured to transmit a signal representing motion of the sensor; and a signal processor, configured to analyse first and second data sets received via the receiver from the motion sensor, the first and second data sets representing respective first and second oscillatory mechanical responses of first and second muscles of the subject resulting from mechanical stimuli, wherein the analysis comprises determining first and second parameter sets characterising the first and second oscillatory mechanical responses, and comparing the first parameter set with the second parameter set to assess a possible presence of DVT in the subject.

In a further aspect, the invention provides an analysis method for assessing a subject at risk of DVT, the method comprising the steps of:

receiving a first data set representing an oscillatory mechanical response of a first muscle of the subject resulting from a first applied mechanical stimulus;

receiving a second data set representing an oscillatory mechanical response of a second muscle of the subject resulting from a second applied mechanical stimulus;

analysing the first and second data sets to determine corresponding first and second parameter sets characterising the first and second oscillatory mechanical response respectively; and comparing the first parameter set with the second parameter set to assess a possible presence of DVT in the subject.

In a still further aspect, the invention provides a method of assessing a subject at risk of DVT, comprising the steps of:

applying a mechanical stimulus to a first muscle of the subject, resulting in an oscillatory mechanical response of the first muscle;

acquiring a first data set representing the oscillatory mechanical response of the first muscle, and analysing the first data set to obtain a first parameter set characterising the oscillatory mechanical response;

applying a mechanical stimulus to a second muscle of the subject, resulting in an oscillatory mechanical response of the second muscle;

acquiring a second data set representing the oscillatory mechanical response of the second muscle and analysing the second data set to obtain a second parameter set characterising the oscillatory mechanical response; and comparing the first parameter set and the second parameter set to assess possible presence of DVT in the subject.

Further features, benefits and advantages of embodiments of the invention will be apparent from the following description, which is provided by way of example only, and should not be considered as limiting of the scope of the invention as defined in any of the preceding statements, or in the claims appended hereto.

BRIEF DESCRIPTION OF THE DRAWINGS

Embodiments of the invention will now be described with reference to the accompanying drawings, in which like reference numerals indicate like features, and wherein.

DETAILED DESCRIPTION OF EMBODIMENTS

Figure 1:
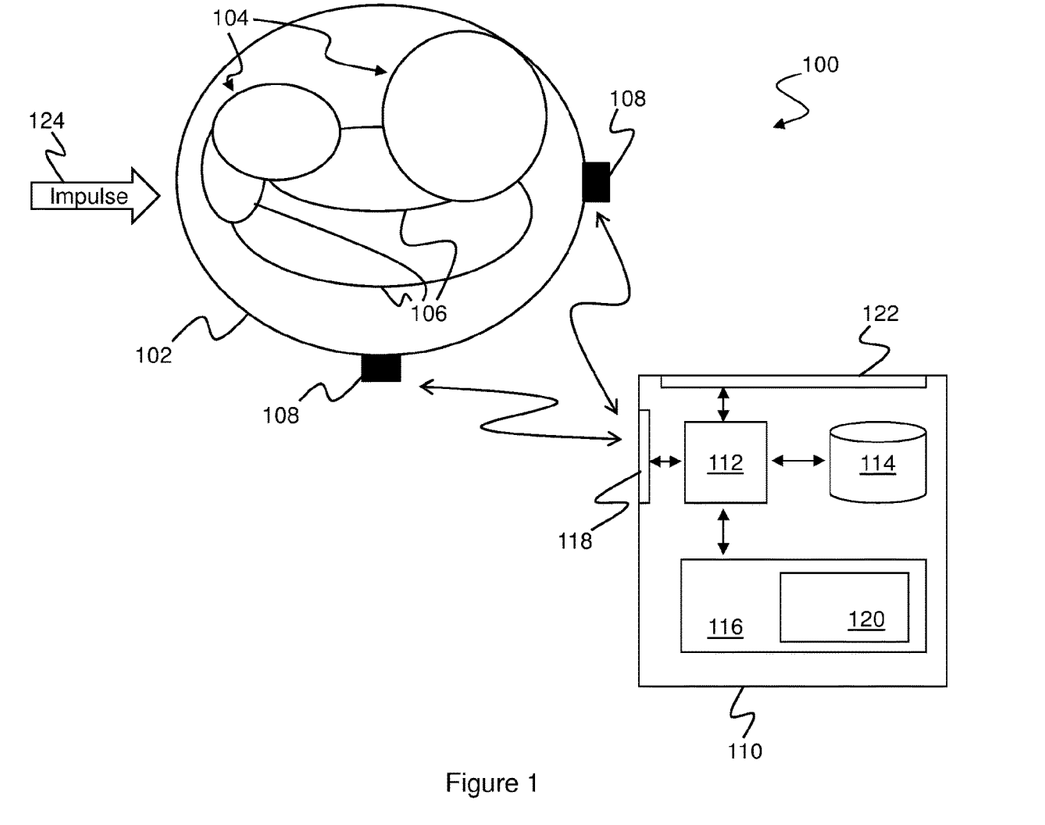
FIG. 1 is a schematic diagram of a system embodying the invention.

FIG. 1 is a schematic diagram of a system 100 embodying the invention. The system 100 captures data sets obtained by applying mechanical stimuli to muscles of a subject. Shown schematically in FIG. 1 is a cross-section through the lower leg 102 of a subject, comprising bones 104 (i.e. fibula and tibia), muscles 106 (i.e. peroneals, tibialis posterior, gastrocnemius, and/or soleus muscles). Collectively, the various muscles making up the back portion of the lower leg are called 'the calf'.

In accordance with the exemplary system 100, one or more motion sensors 108 are fixed to the exterior of the limb, e.g. at the rear and/or side of the calf. In some embodiments of the invention, a single motion sensor, such as a multi-axis accelerometer, may be sufficient. It may be advantageous to provide multiple motion sensors to enable data from each to be combined and/or selection of signals from a sensor providing the strongest or cleanest signal.

The system 100 further includes signal processing apparatus 110, which is configured to receive and analyse information captured by the motion sensor, or sensors, 108. As shown in FIG. 1, the signal processor 110 comprises a combination of hardware and software, in which the hardware and/or the software are configured to embody various features of the invention. The signal processing apparatus 110 may comprise a standard hardware configuration, such as a personal computer, a smartphone or other portable device, or any other suitable computing and communications platform. Alternatively, the signal processing apparatus 110 may comprise custom or semi-custom hardware, including programmable components such as microprocessors, or programmable-logic devices such as a field programmable gate array (FPGA). Where programmable-logic devices are used, these may be configured to include functional blocks implementing features of discrete devices, such as microprocessors, memory devices, and custom analog and/or digital components. As will be appreciated by electronics system designers and engineers, various hardware and/or software implementation options are available, falling within the scope of the present invention.

The exemplary signal processor 110, as illustrated in FIG. 1, comprises a microprocessor component or functional block 112. The microprocessor 112 is interfaced to, or otherwise operably associated with, a non-volatile memory/storage device 114. The non-volatile storage 114 may be a hard disk drive (e.g. if the signal processor 110 is implemented using a personal computer), or may include a solid-state non-volatile memory, such as read-only memory (ROM), flash memory, or the like. The microprocessor 112 is also interfaced to volatile storage 116, such as random access memory (RAM) which contains program instructions and/or transient data relating to the operation of the signal processor 110.

In a conventional configuration, the non-volatile storage device 114 maintains program and data content relevant to the normal operation of the signal processing apparatus 110. For example, if the apparatus 110 is implemented using a personal computer, smartphone, or the like, the storage device 114 may contain operating system programs and data, as well as other executable application software necessary to the intended functions of the signal processing apparatus 110. The storage device 114 may also contain program instructions which, when executed by the microprocessor 112, instruct the apparatus 110 to perform operations in accordance with an embodiment of the present invention, for assessing a subject at risk of DVT. In operation, instructions and data held in non-volatile storage 114 may be transferred to volatile memory 116 as required.

The microprocessor 112 is also operably associated with a communications interface 118 in a conventional manner. The communications interface 118 enables communication between the signal processor 110 and the one or more motion sensors 108. Communications between the signal processing apparatus 110 and each motion sensor 108 may be via a wired connection, such as a Universal Serial Bus (USB) connection, or may be via a wireless connection, such as a Bluetooth, Bluetooth Low Energy (BLE), Wi-Fi, or other wireless communications channel. In the exemplary embodiment of the system 100, communication is conducted via a wireless BLE channel.

In use, the volatile storage 116 includes a corresponding body 120 of program instructions configured to perform processing and operations embodying features of the present invention, as described in greater detail below, particularly with reference to FIGS. 4 to 7.

The signal processing apparatus 110 further includes a display 122 interfaced with the microprocessor 112, enabling information to be communicated to an operator of the apparatus 110. As shown in FIG. 1, the display 122 is integrated with the apparatus 110, and may be, for example, a touchscreen display of a smartphone or similar device. Alternatively, the display 122 may be incorporated into a custom- or semi-custom-designed signal processing apparatus 110. In still other embodiments, the display 122 may be the display of a personal computer, a tablet device, a notebook, or other similar conventional computing platform.

Figure 2:
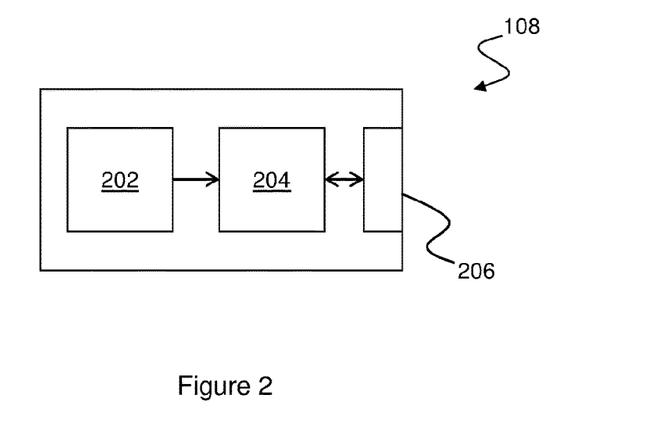
FIG. 2 is a schematic diagram of a motion sensor suitable for use in the system of FIG. 1.

FIG. 2 is a schematic diagram of a motion sensor suitable for use in the system of FIG. 1. The exemplary motion sensor 108 comprises an accelerometer 202, a local processor 204, and a communications interface 206.

Various commercially available components may be used in the design and implementation of the motion sensor 108. For example, the motion sensor 202 may be the part number KXTJ9 Tri-axis Accelerometer, available from Kionix Incorporated of Ithaca, N.Y. The local processor 204 may comprise part number CC2541, Bluetooth Low Energy and Proprietary System-on-Chip, available from Texas Instruments Incorporated of Dallas Tex. The CC2541 part comprises all of the components necessary to communicate with the accelerometer 202, and to implement a wireless BLE communications interface for transmitting accelerometer data to the signal processor 110. The CC2541 part requires only an external antenna 206 for transmitting and receiving BLE signals at 2.4 GHz.

A more complete off-the-shelf motion sensor 108 may be obtained from corporations such as Texas Instruments, in the form of components such as the CC2541 SensorTag reference design, which is a 'development kit' comprising the CC2541 System-on-Chip, the KXTJ9 Accelerometer, along with additional sensors for detecting and recording movement, magnetic fields, humidity, pressure and temperature. The SensorTag reference design is configured for communications with smartphones and other mobile devices executing either the android or iOS operating systems. It is supported by software development tools, and the ability to download software/firmware updates directly from a smartphone or other device. Accordingly, although the SensorTag reference design incorporates sensors that may not be required in a basic implementation of the invention, it provides a convenient development platform for motion sensors 108 embodying the invention.

Figure 3:
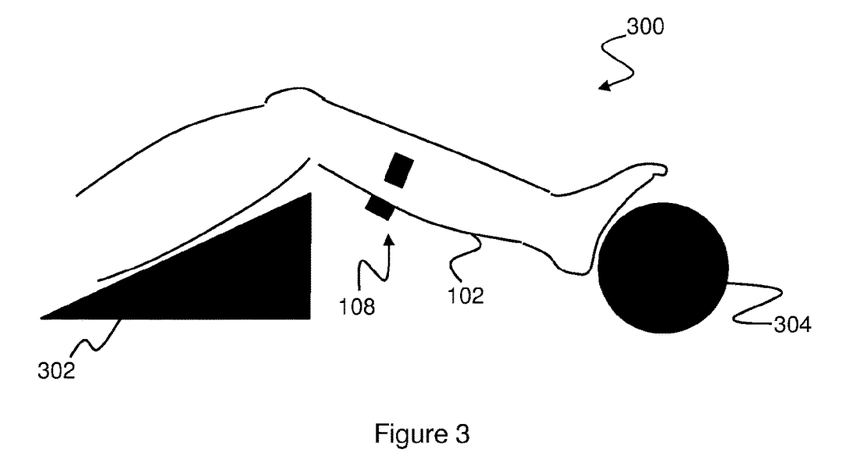
FIG. 3 is a diagram illustrating position and support of a leg of a subject arranged for testing by the system of FIG. 1.

FIG. 3 is a schematic diagram illustrating exemplary position and support of a leg 300 of a subject, arranged for testing using the system 100 of FIG. 1. Supports 302, 304 are provided for the upper leg and foot, respectively, and one or more motion sensors 108 are fixed, e.g. via a strap, tape or other suitable fixing mechanism, to the lower leg 102. The arrangement of supports 302, 304 is provided by way of example only, and other arrangements are possible, e.g. the provision of upper leg support 302 may be optional. In this position, the subject may relax his or her calf muscle, such that a trained technician, clinician, or other healthcare worker may apply a mechanical stimulus, such as a percussive impulse (represented by arrow 124 in FIG. 1) resulting in an oscillatory mechanical response of the subject's calf muscles. The oscillatory mechanical response causes corresponding voltages to be generated along the tri-axis detectors within the accelerometer 202. In the case of the KXTJ9 accelerometer part, the voltages are digitised on-chip, at a selectable resolution of 8, 12 or 14 bits, and transferred to the local processor 204 via an inter-integrated circuit ($I^2C$) standard communications interface. The local processor 204 is programmed to collect, format and transmit the data set corresponding with the digitally sampled accelerometer readings via the transmitter 206 to the receiver 118 of the signal processor 110. In an exemplary embodiment, the BLE communications channel supports a sampling rate of about 800 samples per second, using a 12-bit resolution. Increasing the bandwidth of the communications channel, and/or improving the efficiency of transmission (e.g. by compressing the transmitted data) may enable higher resolution data acquisition, such as one kilosamples/s at up to 14 bits per sample.

As noted above, in the exemplary embodiment a tri-axis accelerometer is employed. This provides motion information, in the form of voltage levels representing acceleration, along three orthogonal axes. Embodiments of the invention may utilise acquired data from a single axis (e.g. the axis providing the strongest signal), or may combine data from multiple axes by computing a resultant magnitude of the acceleration vector. Computation of the magnitude of the acceleration vector may be implemented by software executing on the local processor 204, or on the signal processing apparatus 110. Advantageously, computing the resultant acceleration vector magnitude at the local processor 204 reduces the volume of information that must be transmitted via the BLE communications link from the motion sensor 108 to the signal processor 110.

Figure 4:
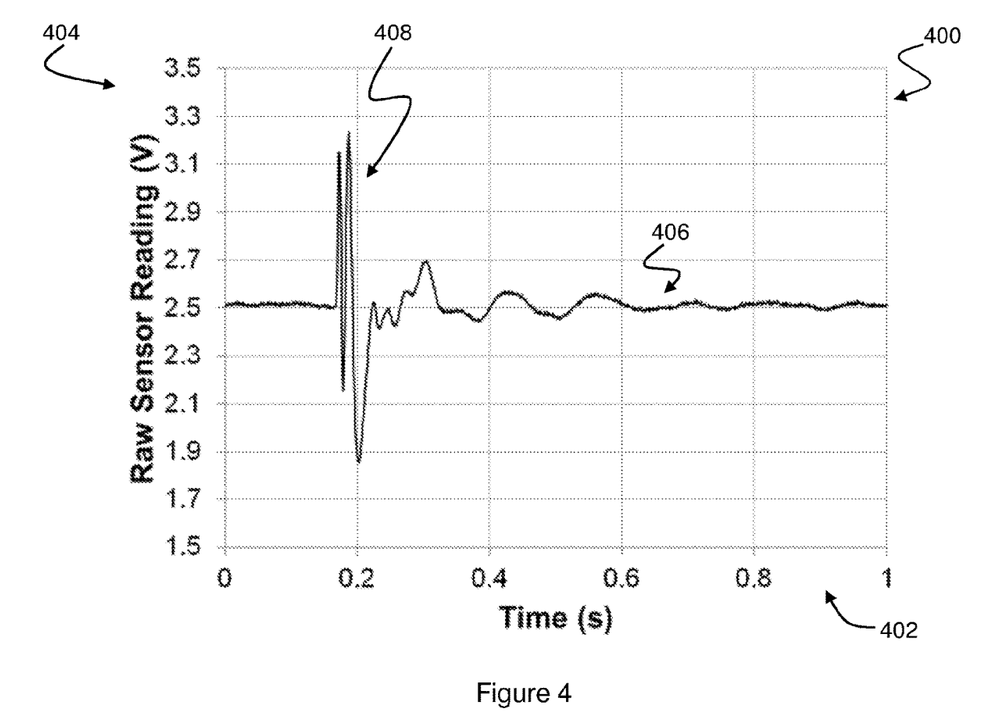
FIG. 4 is a graph of a motion sensor data set representing an exemplary mechanical response obtained according to an embodiment of the invention.

FIG. 4 shows a graph 400 of a motion sensor data set representing an exemplary oscillatory mechanical response obtained using the arrangement and apparatus described above with reference to FIGS. 1 to 3. Time is represented on the horizontal axis 402, while the accelerometer voltage level corresponding with the resultant acceleration magnitude is represented on the vertical axis 404. As can be seen from the resulting acquired data trace 406, a mechanical percussive impulse is applied after approximately 0.17 seconds, resulting in a generally oscillatory motion of the subject's calf, apparent in the portion 408 of the trace 406. This motion substantially settles over a period of approximately 0.8 seconds. A low level of additive noise is also visible, particularly on the steady state portions of the trace 406. The goal of analysis of the oscillatory mechanical response of the subject's calf can therefore be defined as extracting a relevant parameter set, useful for assessing the possible presence of DVT, from the acquired data, in the presence of additive noise.

According to exemplary embodiments of the invention, a starting assumption for the analysis, which may be performed using suitably configured software, firmware and/or hardware implemented on the signal processing apparatus 110, is that the acquired data set 406 may be represented as a superposition of two or more exponentially decaying sinusoidal waveforms. On this assumption, a waveform such as the trace 406 may generally be represented in the following form:

$$V(t) = \sum_{i=1}^{N} A_i e^{-\gamma_i t} \cos(\omega_i t + \phi_i) + n(t)$$

In the above equation, N represents the number of exponentially decaying sinusoidal components to be used in fitting the acquired data set 406. Experiments conducted by the inventors have indicated that N=3 is generally a suitable choice. Each component also has an amplitude A, a characteristic frequency $\omega$, an associated phase $\Phi$, and a damping coefficient $\gamma$. The function n(t) represents the additive noise. It should also be noted that, for the purposes of analysis, the signal is a discrete time sequence of samples of the motion sensor voltage.

Various techniques are available for analysing signals such as that shown in the graph 400 of FIG. 4. For example, Fourier analysis could be employed, based upon the Fast Fourier transform (FFT). However, the FFT may suffer from limited frequency resolution, spectral leakage, picket fence effect, and scalloping loss. While these may be mitigated through choice of proper apodisation, averaging, zero padding, up-sampling, and other well-known approaches, the use of FFT-based methods for analysis of short, aperiodic, signals is likely to be suboptimal.

An alternative technique would be to use a nonlinear regression technique, such as nonlinear least-squares fitting, in order to estimate the unknown parameters of the above equation. Such general techniques may be unstable or unreliable in the presence of additive noise, and may perform poorly when fitting large numbers of unknown parameters. Accordingly, it may be preferable to employ more-targeted techniques for fitting or estimating the parameters of a sum of exponentially decaying sinusoids in the presence of additive background noise. One such targeted technique is Prony's method, however it has been shown that better performance can be obtained using a Matrix Pencil Method (MPM) as described in Hua and Sarkar, 'Matrix Pencil Method for estimating parameters of exponentially damped/undamped sinusoids in noise', *IEEE Transactions on Acoustics, Speech and Signal Processing*, Volume 38, No. 5, May 1990.

Figure 5:
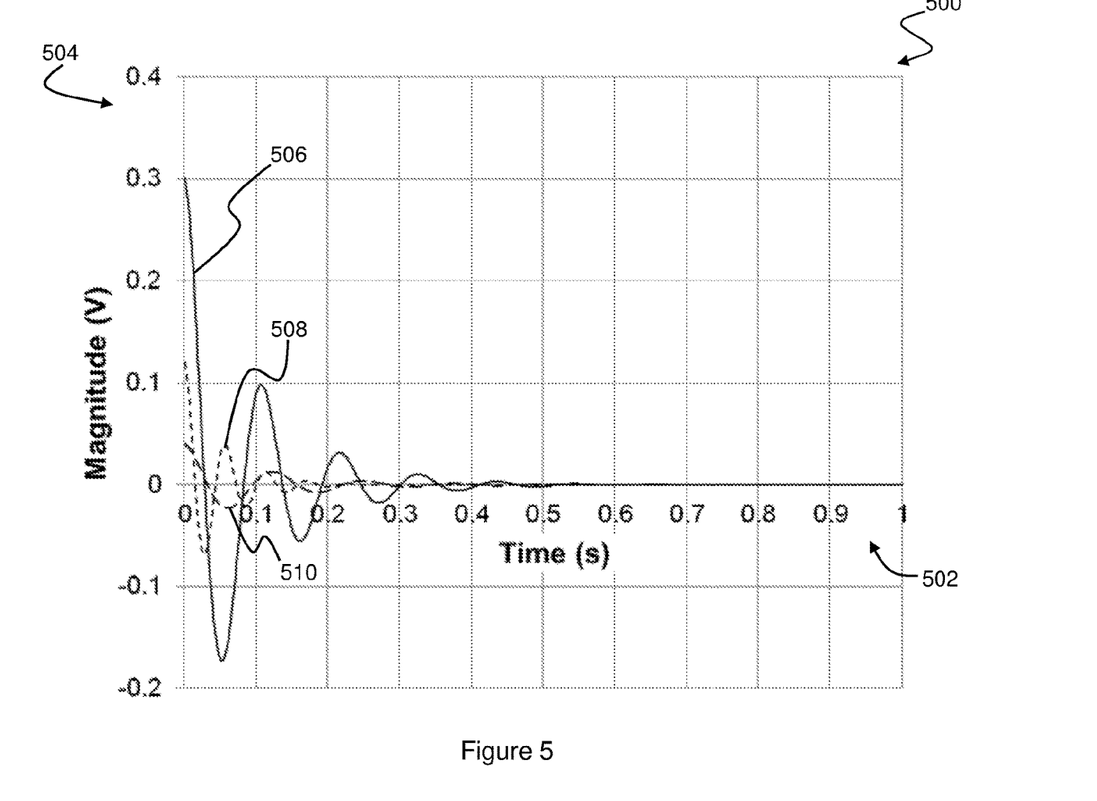
FIG. 5 is a graph illustrating decomposition of a data set into three decaying sinusoidal components according to an embodiment of the invention.

Using the MPM technique, a generally damped oscillatory response, such as the trace 406 shown in the graph 400, may be represented as a superposition of a plurality of exponentially-damped sinusoids, in accordance with the above equation, as illustrated by the graph 500 shown in FIG. 5. Again, the horizontal axis 502 represents time, while the vertical axis 504 represents the equivalent acceleration amplitude in volts, relative to the steady state reading. The acquired data set has been decomposed into three oscillatory components, comprising a dominant component 506, and two smaller components, 508, 510. By design, the MPM technique minimises error due to noise, and thus any further exponentially decaying sinusoidal components would necessarily be of smaller magnitude relative to the three components 506, 508, 510 shown in the graph 500. It is, accordingly, apparent that the inclusion of additional components in the analysis would be of minimal benefit. Indeed, increasing the number of parameters to be estimated may impact upon the stability and reliability of the analysis method.

A key insight of the present inventors is that the mechanical response of a muscle is altered in the presence of DVT. While there is considerable variation between muscles of different subjects, the expected variation between corresponding muscles of pairs of limbs of a single subject is expected to be considerably smaller. Therefore, the possible presence of DVT in one muscle of a subject, such as the right calf muscle, may be assessed by comparison with the corresponding muscle of the other limb, e.g. the left calf muscle. As described below, with reference to FIGS. 6 and 7, a suitable comparison may be made using parameter sets derived from analysis, such as described above, of the mechanical response of each muscle.

According to embodiments of the present invention a parameter set is derived from each data set using MPM analysis. The characteristic frequencies and damping coefficients (or, equivalently, damping factors) of the principal exponentially decaying sinusoidal component have been found to comprise useful parameter sets for the purpose of comparison. Highly statistically significant differences in these parameters have been identified in subjects experiencing DVT in one calf muscle.

Figure 6:
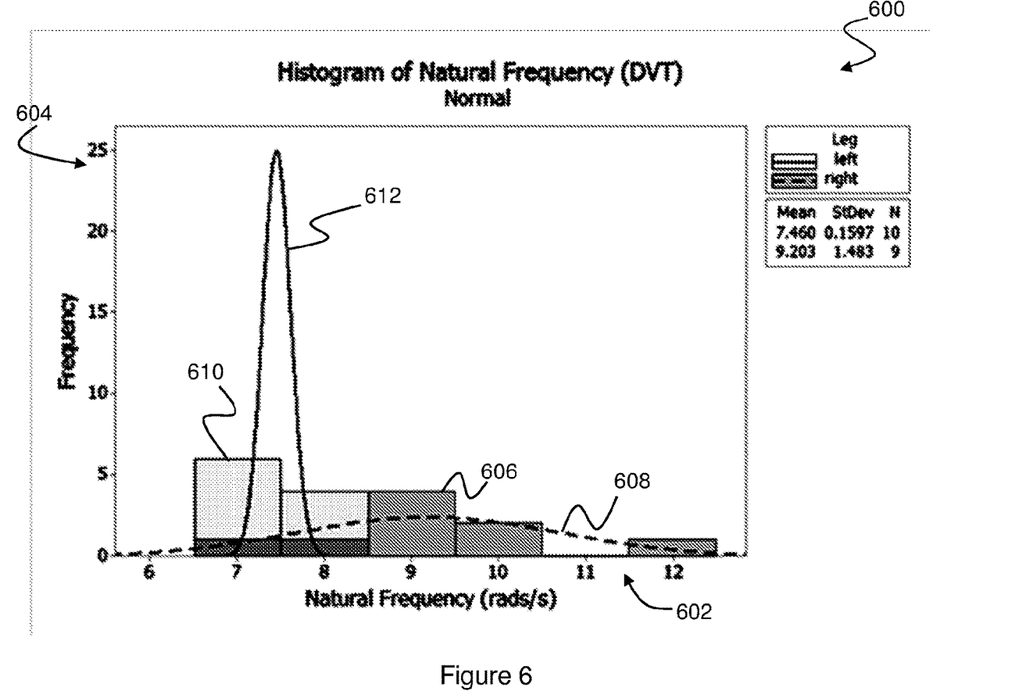
FIG. 6 is a chart illustrating an illustrative statistical analysis of frequency parameters obtained in accordance with an embodiment of the invention.

By way of example, FIG. 6 is a chart 600 illustrating a preliminary statistical analysis of characteristic frequency parameters obtained in accordance with an embodiment of the invention. The horizontal axis 602 of the chart shows the characteristic frequency (in radians per second), while the vertical axis 604 represents the number of events (out of 10 repeated tests for the left leg, and nine for the right), falling within each identified characteristic frequency band. The result of this analysis is a histogram 606 for the left leg of the subject, to which a corresponding normal distribution curve 608 has been fitted, and a further histogram 610 for the right leg, to which a corresponding normal distribution curve 612 has been fitted. In this particular case, the subject is known, from other tests, to have DVT in the right calf muscle, but not in the left calf muscle. The reduction in the characteristic frequency resulting from the presence of the DVT is statistically significant, having a p-value of 0.01 (i.e. less than 0.05) when analysed using the statistical t-test.

Figure 7:
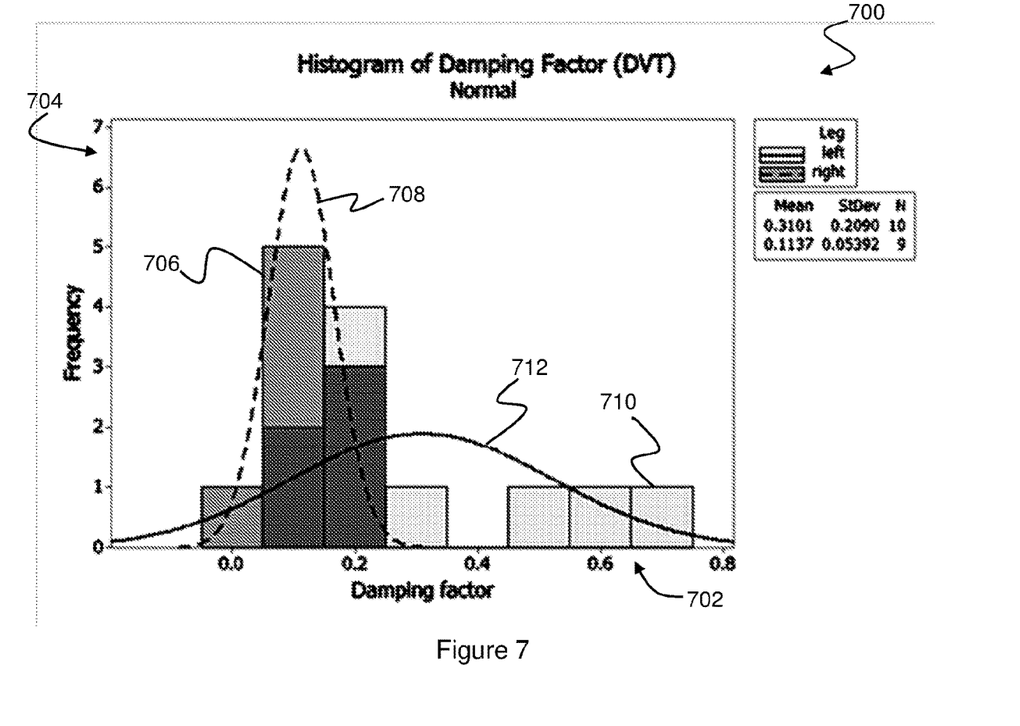
FIG. 7 is a chart illustrating an illustrative statistical analysis of damping parameters obtained in accordance with an embodiment of the invention.

FIG. 7 shows a similar chart 700 resulting from a preliminary statistical analysis of damping factors. In this case, the horizontal axis 702 represents damping factor, while the vertical axis 704 once again shows the number of events within each identified damping factor range obtained from a sample of 10 repeated mechanical stimulus impacts. A histogram 706 representing damping factors for the left calf muscle has been fitted with a corresponding normal distribution curve 708, while a histogram 710 corresponding with damping factors for the right calf muscle has been fitted with a normal distribution curve 712. There is, once again, a clear difference between the left and right calf muscle response, and t-test analysis has established that the difference is statistically significant, having a p-value of 0.02. It is clear that a higher damping factor is observed in the muscle having DVT.

In accordance with embodiments of the invention, the above analysis may be performed by the signal processor 110, and graphs such as the response 400 shown in FIG. 4, and results of statistical analyses such as the charts 600, 700 shown in FIG. 6 or 7, rendered on the display 122. An operator, i.e. a trained technician, clinician or other healthcare worker, will thus be able to assess the possible presence of DVT in the subject of the test by visual inspection of the displayed results.

According to some embodiments of the invention, the statistical analysis may be used in further comparisons performed by the signal processor 110 in order to offer the operator a preliminary assessment of likelihood of the presence of DVT. For example, based upon the analysis of aggregate data using computational and statistical methods including, but not confined to, logistic regression, the results may be used to assess the differences in characteristic frequency and/or damping factor between a series of tests performed on left and right calf muscles of the subject. If the likelihood or probability of the differences is above a clinically and empirically determined threshold (or any other desired criterion, depending upon requirements) then the signal processor 110 may highlight to the operator the likelihood or probability that DVT is present, and identify the relevant muscle.

Advantageously, therefore, embodiments of the invention provide a useful diagnostic tool that may be used by healthcare workers to identify patients having a high likelihood of DVT. Such patients may then be referred for further testing and diagnosis. Used as a preliminary test, embodiments of the invention may be able to eliminate the likelihood that DVT is present in individual subjects, thus avoiding the need for unnecessary further testing, which may be costly, invasive and inconvenient.

While particular embodiments and variations of the invention have been described herein, further modifications and alternatives will be apparent to persons skilled in the relevant art. For example, while the system described with reference to FIGS. 1 and 2 employs a motion sensor 108 which performs data acquisition and digital transmission, along with a signal processing apparatus 110 that receives the digital signals and performs further processing and analysis, other arrangements are also possible. For example, additional analysis and processing could be performed on-board the motion sensor unit 108. Furthermore, a wired, rather than a wireless, connection may be provided between the motion sensor unit 108 and the signal processing apparatus 110. Furthermore, analog signals may be obtained by the motion sensor, e.g. voltage representing acceleration or other motion parameters, and transmitted in analog form to the signal processing apparatus 110, which would receive and digitise the analog signals. Various combinations and arrangements of the above alternatives are also possible, and fall within the scope of the present invention.

In other variations, alternative forms of analysis may be employed to determine parameter sets characterising muscle response to mechanical stimuli, such as modal analysis.

Accordingly, the particular embodiments described in detail should be understood as provided by way of example, for the purpose of teaching the general features of the invention, but should be understood as not limiting of the scope of the invention, which is defined in the following claims.

The invention claimed is:

1. A system for assessing a subject at risk of deep vein thrombosis (DVT), comprising:
    at least one motion sensor, adapted to be fixed, in use, to at least one of a first muscle and a second muscle of the subject, the motion sensor including a transmitter configured to transmit a signal representing motion of the sensor;
    a receiver, configured to receive the signal from the transmitter of the motion sensor; and
    a signal processor, coupled to the receiver, and configured to analyse first and second data sets received via the receiver from the at least one motion sensor, the first data set representing a first decaying oscillatory mechanical response of the first muscle of the subject resulting from a first percussive mechanical impulse applied to the first muscle while suspended in a relaxed and unsupported state, the second data set representing a second decaying oscillatory mechanical response of the second muscle of the subject resulting from a second percussive mechanical impulse applied to the second muscle while suspended in a relaxed and unsupported state, wherein the analysis comprises:
        determining a first parameter set characterizing the first decaying oscillatory mechanical response,
        determining a second parameter set characterizing the second decaying oscillatory mechanical response, and
        comparing the first parameter set with the second parameter set to identify differences therebetween, indicative of a possible presence of DVT in the subject.

2. The system of claim 1 wherein the first and second muscles are corresponding muscles of respective left and right limbs of the subject.

3. The system of claim 1 wherein the first and second muscles are corresponding muscle groups in a calf muscle of a left leg of the subject and a calf muscle of a right leg of the subject.

4. The system of claim 1 wherein the analysis comprises decomposing the decaying oscillatory mechanical responses of the first and second muscles, such that the first and second parameter sets each comprise at least one frequency parameter and at least one corresponding damping parameter characterising the respective decaying oscillatory mechanical response.

5. The system of claim 4 wherein the first and second parameter sets each comprise frequency parameters and corresponding damping parameters of two or more decaying oscillatory components of the mechanical responses of the first and second muscles of the subject.

6. The system of claim 4 wherein the possible presence of DVT in the subject is assessed by the signal processor based on a difference between the frequency parameters and/or the damping parameters of the first and second parameter sets.

7. The system of claim 1 wherein, for the purpose of comparing the first parameter set with the second parameter set, the signal processor is configured to present information relating to the first and second parameter sets on a display.

8. The system of claim 1 wherein the signal processor is configured to perform further statistical analysis of the first and second parameter sets, obtained over multiple responses of the first and second muscles of the subject to multiple percussive mechanical impulses, in order to assess a statistical significance of differences between the first and second parameter sets, and to provide a specific indication of the presence of DVT or other soft tissue abnormality in the subject.

9. The system of claim 1 wherein the motion sensor comprises an accelerometer.

10. The system of claim 1 wherein a communications channel between the transmitter and the receiver comprises a wired connection.

11. The system of claim 1 wherein a communications channel between the transmitter and the receiver comprises a wireless connection.

12. An apparatus for assessing a subject at risk of deep vein thrombosis (DVT), comprising:
a receiver, configured to receive a signal from a transmitter associated with at least one motion sensor, wherein the motion sensor is adapted to be fixed, in use, to at least one of a first muscle and a second muscle of the subject, and is configured to transmit a signal representing motion of the sensor; and
a signal processor, configured to analyse first and second data sets received via the receiver from the at least one motion sensor, the first data set representing a first decaying oscillatory mechanical response of the first muscle of the subject resulting from a first percussive mechanical impulse applied to the first muscle while suspended in a relaxed and unsupported state, the second data set representing a second decaying oscillatory mechanical response of the second muscle of the subject resulting from a second percussive mechanical impulse applied to the second muscle while suspended in a relaxed and unsupported state, wherein the analysis comprises:
determining a first parameter set characterizing the first decaying oscillatory mechanical response,
determining a second parameter set characterizing the second decaying oscillatory mechanical response, and
comparing the first parameter set with the second parameter set to identify differences therebetween, indicative of a possible presence of DVT in the subject.

13. An analysis method for assessing a subject at risk of deep vein thrombosis (DVT), the method comprising the steps of:
receiving a first data set representing a first decaying oscillatory mechanical response of a first muscle of the subject resulting from a first percussive mechanical impulse applied to the first muscle while suspended in a relaxed and unsupported state;
receiving a second data set representing a second decaying oscillatory mechanical response of a second muscle of the subject resulting from a second percussive mechanical impulse applied to the second muscle while suspended in a relaxed and unsupported state;
analyzing the first data set to determine a corresponding first parameter set characterizing the first decaying oscillatory mechanical response;
analyzing the second data set to determine a second parameter set characterizing the second decaying oscillatory mechanical response; and
comparing the first parameter set with the second parameter set to identify differences therebetween, indicative of a possible presence of DVT in the subject.

14. A method of assessing a subject at risk of deep vein thrombosis (DVT), comprising the steps of:
applying a first percussive mechanical impulse to a first muscle of the subject while the first muscle is suspended in a relaxed and unsupported state, resulting in a first decaying oscillatory mechanical response of the first muscle;
acquiring a first data set representing the first decaying oscillatory mechanical response of the first muscle, and analysing the first data set to obtain a first parameter set characterising the first decaying oscillatory mechanical response;
applying a second percussive mechanical impulse to a second muscle of the subject while the second muscle is suspended in a relaxed and unsupported state, resulting in a second decaying oscillatory mechanical response of the second muscle;
acquiring a second data set representing the second decaying oscillatory mechanical response of the second muscle, and analysing the second data set to obtain a second parameter set characterising the second decaying oscillatory mechanical response; and
comparing the first parameter set and the second parameter set to identify differences therebetween, indicative of a possible presence of DVT in the subject.

* * * * *

UNITED STATES PATENT AND TRADEMARK OFFICE
CERTIFICATE OF CORRECTION

PATENT NO. : 11,076,761 B2
APPLICATION NO. : 15/519264
DATED : August 3, 2021
INVENTOR(S) : Laurence Simpson et al.

Page 1 of 1

It is certified that error appears in the above-identified patent and that said Letters Patent is hereby corrected as shown below:

On the Title Page

In the "(71) Applicants" section:
Please delete: Epworth Research Institute,
Richmond (AU); La Trobe University,
Bundoora (AU); Laurence Simpson,
Richmond (AU); Lawrie Knuckey,
Richmond (AU)

And please replace it with:
Kynetyka Technologies Pty Ltd, Victoria (AU);
Lawrie Knuckey, Richmond (AU)

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*